(12) United States Patent
Warashina et al.

(10) Patent No.: US 8,394,798 B2
(45) Date of Patent: Mar. 12, 2013

(54) COMPOSITIONS AND METHODS FOR INDUCING NEURONAL DIFFERENTIATION

(75) Inventors: Masaki Warashina, Tsukuba (JP); Kyung Hoon Min, San Diego, CA (US); Fred Gage, La Jolla, CA (US); Peter Schultz, La Jolla, CA (US); Sheng Ding, La Jolla, CA (US); Tomoko Kuwabara, Tsukuba (JP)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/356,079

(22) Filed: Jan. 23, 2012

(65) Prior Publication Data

US 2012/0157457 A1    Jun. 21, 2012

Related U.S. Application Data

(62) Division of application No. 12/095,723, filed as application No. PCT/US2006/046009 on Dec. 1, 2006, now Pat. No. 8,105,581.

(60) Provisional application No. 60/741,733, filed on Dec. 1, 2005.

(51) Int. Cl.
*A01N 65/00* (2009.01)
*A61K 35/12* (2006.01)
*A61P 25/00* (2006.01)

(52) U.S. Cl. ............ 514/236.8; 435/378; 435/377; 435/29; 435/325; 435/354; 514/370; 544/133; 548/193; 548/194

(58) Field of Classification Search ............ 424/93.7; 435/378, 377, 29, 325, 354, 6; 514/236.8, 514/371; 544/133; 548/193, 194
See application file for complete search history.

(56) References Cited

U.S. PATENT DOCUMENTS

2005/0119320 A1    6/2005   Bruce et al.

FOREIGN PATENT DOCUMENTS

| WO | WO 2004/033439 A1 | 4/2004 |
| WO | WO 2005/035510 A1 | 4/2005 |
| WO | WO 2005/070042 A2 | 8/2005 |

OTHER PUBLICATIONS

Chinone et al., "The Reactions of 4-Aminothiazolium Salts with Amines," Bulletin of the Chemical Society of Japan, 1972, vol. 45, pp. 2222-2223.
EP Application No. 06 83 8788, Supplementary Partial European Search Report, dated Dec. 12, 2011, 8 pages.
Firestone et al., ACS Chemical Biology, vol. 5(1):2010, pp. 15-34.
Warashina et al., Neurochemistry, Angewandte Chemie, 2006, vol. 45, pp. 591-593.
International Search Report mailed on Mar. 19, 2007, for PCT Application No. PCT/US2006/046009, filed on Dec. 1, 2006, one page.

*Primary Examiner* — Savitha Rao
(74) *Attorney, Agent, or Firm* — Kilpatrick Townsend & Stockton LLP (57) ABSTRACT

The present invention provides compositions and methods for inducing neuronal cell differentiation.

15 Claims, 4 Drawing Sheets

COMPOSITIONS AND METHODS FOR INDUCING NEURONAL DIFFERENTIATION

RELATED APPLICATIONS

Not applicable.

BACKGROUND OF THE INVENTION

Neurodegenerative diseases and disorders affect millions of people every year. Such diseases include, Alzheimer's Disease, Parkinson's Disease, Multiple Sclerosis, Amyotrophic Lateral Sclerosis (ALS or Lou Gehrig's Disease), Huntington's Disease, Frontotemporal Dementia (Pick's Disease), Prion Diseases, as well as neural diseases and disorders resulting from trauma to the central or peripheral nervous system.

Accordingly, there is considerable interest in the development of stem cell-based therapies for neurodegenerative disease (Abrous et al., *Physiol. Rev.* 85:523-569 (2005); Picard-Riera et al., *J. Neurosci. Res.* 76:223-231 (2004); Shors et al., *Nature,* 410:372-376 (2001); Lie, D. C. et al., *Annu. Rev. Pharmacol. Toxicol.* 44:399-421 (2004); Jin, K. et al., *Proc. Natl. Acad. Sci. USA,* 101:343-347 (2004)). However, the molecular mechanisms underlying stem cell fate specification are still poorly understood, and current methods are do not selectively induce differentiation of neural stem cells or neural progenitor cells into neuronal cells. While several agents, including retinoic acid (RA) (Eriksson, P. S. et al., *Nature Med.* 4:1313-1317 (1998); Palmer, T. D. et al., *Mol. Cell Neurosci.,* 8:389-404 1997), leukemia inhibitory factor (LIF) (Nakashima, K. et al., *Science* 284:479-482 (1999)) and insulin-like growth factor-1 (IGF-1 (Hsieh, J. et al., *J Cell Biol.* 164:111-122 (2004)), have been found to direct neuronal, astroglial and oligodendrocytic differentiation, each of these agents are either pleiotropic or have poor activity in vivo.

Thus, there is a need in the art for compositions and methods for inducing selective differentiation of stem cells (e.g., neural stem cells and neuronal progenitor cells) into neurons, both in vivo and in vitro. Moreover, there is a particular need for small molecules that can induce selective differentiation of stem cells into neuronal cells in vivo and in vitro. The present invention satisfies these and other needs.

SUMMARY OF THE INVENTION

The present invention provides compositions and methods for inducing neuronal differentiation. The compounds of the present invention include all pharmaceutically acceptable salts, isomers, solvates, hydrates and prodrugs thereof.

In one aspect, the present invention provides compounds having the structure of Formula I:

I and pharmaceutically acceptable salts and hydrates thereof.

In Formula I, $R^1$, if present, is a functional group including, but not limited to, $C_{1-8}$ alkyl, $C_{1-8}$ haloalkyl, $C_{3-8}$ cycloalkyl, $C_{2-8}$ alkenyl, $C_{2-8}$ alkynyl, halogen, $-NO_2$, $-CN$, $-OR^a$, $-SR^a$ and $-NR^aR^b$, wherein $R^a$ and $R^b$ are each independently a functional group including, but not limited to, hydrogen, $C_{1-6}$ alkyl, $C_{1-6}$ haloalkyl, $C_{3-8}$ cycloalkyl, aryl-$C_{0-6}$ alkyl and heteroaryl-$C_{0-6}$ alkyl, or when $R^a$ and $R^b$ are attached to the same nitrogen, $R^a$ and $R^b$ can be optionally combined to form a 5- to 7-member heterocycloalkyl ring having from 1-3 heteroatoms including, but not limited to, N, O and S. For example, when $R^a$ and $R^b$ are attached to the same nitrogen atom, $R^a$ and $R^b$ can be combined to form a pyrrolidine, pyrrolidinone, piperidine, or morpholine ring, and the like. In Formula I, $R^2$, if present, is a functional group including, but not limited to, $C_{1-8}$ alkyl, $C_{1-8}$ haloalkyl, $C_{3-8}$ cycloalkyl, $-NO_2$, $-CN$, halogen, $-C(O)R^d$, $-C(O)OR^d$, $-C(O)NR^dR^e$, $-NR^dR^e$, $OR^d$, $SR^d$, and $-NR^dC(O)R^f$, wherein $R^d$ and $R^e$ are each independently a functional group including, but not limited to, hydrogen, $C_{1-6}$ alkyl, $C_{1-6}$ haloalkyl, $C_{3-8}$ cycloalkyl, $C_{2-6}$ alkenyl, aryl-$C_{0-6}$ alkyl and heteroaryl-$C_{0-6}$ alkyl, or when $R^d$ and $R^e$ are attached to the same nitrogen atom, $R^d$ and $R^e$ can be optionally combined to form a 5- to 7-member heterocycloalkyl ring having from 1-3 heteroatoms including, but not limited to, N, O and S. For example, when $R^d$ and $R^e$ are attached to the same nitrogen atom, $R^d$ and $R^e$ can be combined to form a pyrrolidine, pyrrolidinone, piperidine or morpholine ring, and the like. The $R^f$ substituent is a functional group including, but not limited to, $C_{1-6}$ alkyl, $C_{1-6}$ haloalkyl, $C_{3-8}$ cycloalkyl, $C_{2-6}$ alkenyl, $C_{0-6}$ alkyl-aryl and $C_{0-6}$ alkyl-heteroaryl. In Formula I, the subscripts m and n are independently selected and are integers from 0 to 4. In Formula I, $R^3$ is a functional group including, but not limited to, hydrogen, $C_{1-8}$ alkyl, $C_{1-8}$ haloalkyl, $C_{3-8}$ cycloalkyl, $C_{1-8}$ acyl, $-SO_2-C_{1-8}$ alkyl, aryl-$C_{0-4}$ alkyl and heteroaryl-$C_{0-4}$ alkyl. In Formula I, $R^4$, if present, is a functional group including, but not limited to, $C_{1-8}$ alkyl, halogen, $-NO_2$ and $-CN$. In Formula I, the subscript o is an integer from 0 to 1.

In another embodiment, the present invention provides methods of inducing neuronal differentiation. Mammalian cells are contacted with a compound of Formula I, whereupon the mammalian cell differentiates into a neuronal cell. The step of contacting can be in vivo or in vitro. In view of their ability to induce selective differentiation of stem cells (e.g., neural stem cells and neural progenitor cells) into neuronal cells, the compounds of Formula I are useful for treating neural disorders and diseases, such as, e.g., Alzheimer's Disease, Parkinson's Disease, Multiple Sclerosis, Amyotrophic Lateral Sclerosis (ALS or Lou Gehrig's Disease), Huntington's Disease, Frontotemporal Dementia (Pick's Disease), Prion Diseases, as well as neural diseases and disorders resulting from trauma to the central or peripheral nervous system (e.g., partial or complete paralysis, loss of gross and fine motor control, etc.).

Another embodiment of the present invention provides methods of treating neural disorders by contacting a mammalian cell with a compound of Formula I, whereupon the mammalian cell differentiates into a neuronal cell. If the mammalian cell is contacted with a compound of Formula I in vitro, the differentiated cells are administered to an individual with the disorder, thereby treating the disorder. In some embodiments, the mammalian cell is attached to a solid support (e.g., a three-dimensional matrix or a planar surface).

In some embodiments, the mammalian cell is contacted with a compound of Formula I in vivo. If the mammalian cell is contacted with a compound of Formula I in vivo, the step of contacting may be by oral, intravenous, subcutaneous, or intraperitoneal administration of the compound to the mammal.

In some embodiments, the differentiation of the mammalian cell into a neuronal cell is detected. In some embodiments, the differentiation of the mammalian cell into a neuronal cell is detected by detecting expression of an neuronal cell marker (e.g., NeuroD1, NeuN, TuJ1, neurofilament H, or Map2). In other embodiments, the differentiation of the mammalian cell into a neuronal cell is detected by detecting down-regulation of a neural progenitor cell marker (e.g., Sox 2).

In some embodiments, the mammalian cell is a stem cell, (e.g., a neural progenitor cell). In some embodiments, the stem cell is isolated from a rat (e.g., a rat hippocampal progenitor cell) or from a primate (e.g., a human).

Other embodiments and advantages of the present invention will be apparent from the detailed description that follows.

DETAILED DESCRIPTION OF THE INVENTION AND PREFERRED EMBODIMENTS

I. Introduction

The present invention provides compounds, compositions and methods for inducing neuronal cell differentiation. More particularly, the present invention provides compounds of Formula I that are useful for inducing neuronal cell differentiation. In some embodiments, a composition comprising the compound of Formula I is provided. In other embodiments, methods of inducing neuronal cell differentiation in mammalian cells are provided. Neuronal cell differentiation can be induced in vivo or in vitro according to the methods of the present invention.

The compounds of Formula I can be used in therapeutic methods, e.g., to treat or prevent neural diseases and disorders including Alzheimer's Disease, Parkinson's Disease, Multiple Sclerosis, Amyotrophic Lateral Sclerosis (ALS or Lou Gehrig's Disease), Huntington's Disease, Frontotemporal Dementia (Pick's Disease), Prion Diseases as well as neural disorders associated with trauma or injury to the central or peripheral nervous systems (e.g., partial or complete paralysis, loss of gross and fine motor function, etc.). Compounds of Formula I can also be used to probe signaling pathways that regulate neuronal differentiation.

II. Definitions

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Unless otherwise stated, the "cycloalkyl" and "heterocycloalkyl" rings are monovalent radicals. Non limiting examples of heterocycloalkyl groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene", by itself or as part of another substituent, means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quatemized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —CH$_2$—CH$_2$—S—CH$_2$CH$_2$— and —CH$_2$—S—CH$_2$—CH$_2$—NH—CH$_2$—, —O—CH$_2$—CH=CH—, —CH$_2$—CH=C(H)CH$_2$O—CH$_2$— and —S—CH$_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-10 membered ring with the nitrogen atom to which each is attached. The ring may be monocyclic, bicyclic or polycyclic. Accordingly, a group represented as —NR$^a$R$^b$ is meant to include piperidinyl, pyrrolidinyl, 2-oxopyrrolidinyl, morpholinyl, azetidinyl, decahydro-isoquinolinyl, decahydroquinolinyl, tetrahydroquinolinyl and the like.

The terms "halo" or "halogen," by themselves or as part of another substituent, mean, unless Otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Unless otherwise stated, an "aryl" or "heteroaryl" group is a monovalent radical. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like). Addtionally for brevity, the term "aryl-C$_{0-4}$ alkyl" refers to those radical in which the aryl group is directly connected to the remainder of the molecule or is attached through a C$_{1-4}$ alkyl group.

The above terms (e.g., "alkyl," "aryl" and "heteroaryl"), include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R'', —SR', —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R'', —NR'S(O)$_2$R'', —CN and —NO$_2$ in a number ranging from zero to (2 m'+1), where m' is the total number of carbon atoms in such radical. R', R'' and R''' each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R'' are attached to the same nitrogen atom, they can be combined with the nitrogen atom to form a 3-, 4-, 5-, 6-, or 7-membered ring. For example, —NR'R'' is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substitutent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —NR'S(O)$_2$R'', —N$_3$, perfluoro(C$_1$-C$_4$)alkoxy, and perfluoro(C$_1$-C$_4$)alkyl, in a number ranging from zero to the total number of open valences on the aromatic ring system; and where R', R'' and R''' are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

A wavy bond, ⌇, that intersects a single, double, or triple bond in a chemical structure depicted herein, indicates the point of attachment of the single, double, or triple bond to the remainder of the molecule.

As used herein, the terms "ortho", "meta", and "para" can be used to describe the position of a substituent relative to a reference substituent on an aryl ring, such as a phenyl ring, and the like. In such instances, it should be understood that an "ortho" substituent refers to a substituent that is attached to the aryl ring atom adjacent to the ring atom to which the reference substituent is attached. Similarly, a "meta" and "para" substitutent refers to a substituent that is attached to the aryl ring atom two and three ring atoms, respectively, away from the ring atom to which the reference substituent (Ref) is attached. For further clarity, the ortho "o", meta "m" and para "p" positions on a phenyl ring bearing a reference substituent is set forth below:

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylarnine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Neural cell differentiation" or "neuronal differentiation" as used herein, refers to differentiation of stem cells into neurons. i.e., the primary cells of the nervous system. Neurons comprise a dendrite (i.e., a short, branching structure); a soma (i.e., a cell body)l; and an axon (i.e., fine, cable-like projection which may extend tens, hundreds, or even tens of thousands of times the diameter of the soma in length). Axons and dendrites in the central nervous system are typically about 1 μm, while some of those in the peripheral nervous system are much thicker. The soma (i.e., the cell body containing the nucleus) is usually about 25 μm in diameter and about the same size as the cell nucleus. Neurons can be classified into subtypes based on physiological function (i.e., afferent, efferent, or interneurons) or their anatomical structure (i.e., pseudounipolar; bipolar; multipolar; Golgi I; and Golgi II).

A "stem cell," as used herein, refers to any self-renewing pluripotent cell or multipotent cell or progenitor cell or precursor cell that is capable of differentiating into multiple cell types. Stem cells suitable for use in the methods of the present invention are multipotent cells that are capable of differentiating into neuronal cells (i.e., neurons), astrocytes and oligodendrocytes (Eriksson, P. S. et al., *Nature Med.* 4:1313-1317 (1998); Palmer, T. D. et al., *Mol. Cell Neurosci.,* 8:389-404 1997).

"Differentiate" or "differentiation," as used herein, refers to the process by which precursor or progenitor cells (i.e., neural progenitor cells) differentiate into specific cell types, e.g., neuronal cells. Differentiated neuronal cells can be identified by their patterns of gene expression and cell surface protein expression. Typically, neuronal cells express genes such as, for example, and Neuro D1. Typically, neuronal cells express specific transcription factors such as, for example, E2F4 (see, e.g.,). Typically, neural progenitor cells express Sox 2, CD133, and nestin.

A "solid support," as used herein in connection with inducing neuronal differentiation, refers to a three-dimensional matrix or a planar surface on which the stem cells can be cultured. The solid support can be derived from naturally occurring substances (i.e., protein based substances such as collagen, fibrin, and alginate) or synthetic substances including biodegradable polymers such as, e.g., poly-L-lactic acid, and polyglycolic acid). The solid support may incorporate factors that can facilitate cell differentiation (see, e.g., Silva et al., *Science* 303: 1352 (2004)). Suitable synthetic matrices are described in, e.g., U.S. Pat. Nos. 5,041,138, 5,512,474, and 6,425,222. For example, biodegradable artificial polymers, such as polyglycolic acid, polyorthoester, or polyanhydride can be used for the solid support. Polymers such as polypropylene, polyethylene glycol, and polystyrene can also be used in the solid support. Cells cultured and differentiated on a solid support that is a three-dimensional matrix typically grow on all of the surfaces of the matrix, e.g., internal and external. Cells cultured and differentiated on a solid support that is planar typically grow in a monolayer. The term "solid-support" is also used in the context of preparing the compounds of Formula I. In this context, "solid-support" refers to a polymeric support, such as a bead, that can be partially soluble in a suitable solvent or completely insoluble, and is used to bind, for example, a reactant or a reagent of the reaction. Suitable solid-supports include, but are not limited to, PAL resin, Wang resin, and polystyrene resin.

"Culturing," as used herein, refers to maintaining cells under conditions in which they can proliferate, differentiate, and avoid senescence. For example, in the present invention, cultured neural progenitor cells proliferate and differentiate into neuronal cells. Cells can be cultured in growth media containing appropriate growth factors, i.e., a growth factor cocktail that contains, for example, retinoic acid (RA), leukemia inhibitory factor (LIF), and/or insulin-like growth factor-1 (ILGF-1).

III. Compounds of the Present Invention and Methods of Making thereof

A. Compounds of Formula I

In one aspect, the present invention provides for compounds having the structure of Formula I:

and pharmaceutically acceptable salts and hydrates thereof.

In Formula I, $R^1$, if present, is a functional group including, but not limited to, $C_{1-8}$ alkyl, $C_{1-8}$ haloalkyl, $C_{3-8}$ cycloalkyl, $C_{2-8}$ alkenyl, $C_{2-8}$ alkynyl, halogen, $-NO_2$, $-CN$, $-OR^a$, $-SR^a$ and $-NR^aR^b$, wherein $R^a$ and $R^b$ are independently selected and are a functional group including, but not limited to, hydrogen, $C_{1-6}$ alkyl, $C_{1-6}$ haloalkyl, $C_{3-8}$ cycloalkyl, aryl-$C_{0-6}$ alkyl and heteroaryl-$C_{0-6}$ alkyl, or when $R^a$ and $R^b$ are attached to the same nitrogen atom, $R^a$ and $R^b$ can be optionally combined to form a 5- to 7-member heterocycloalkyl ring having from 1-3 heteroatoms selected from the group consisting of N, O and S. For example, $R^a$ and $R^b$, when attached to the same nitrogen atom can form a pyrrolidine, pyrrolidinone, piperidine, or morpholine ring and the like.

In Formula I, $R^2$, if present, is a functional group including, but not limited to, $C_{1-8}$ alkyl, $C_{1-8}$ haloalkyl, $C_{3-8}$ cycloalkyl, $-NO_2$, $-CN$, halogen, $-C(O)R^d$, $-C(O)OR^d$, $-C(O)NR^dR^e$, $-NR^dR^e$, $-S(O)_2NR^dR^e$, $OR^d$, $SR^d$, and $-NR^dC(O)R^f$, wherein $R^d$ and $R^e$ are each independently a functional group including, but not limited to hydrogen, $C_{1-6}$ alkyl, $C_{1-6}$ haloalkyl, $C_{3-8}$ cycloalkyl, $C_{2-6}$ alkenyl, aryl-$C_{0-6}$ alkyl and heteroaryl-$C_{0-6}$ alkyl, or when $R^d$ and $R^e$ are attached to the same nitrogen, $R^d$ and $R^e$ can be optionally combined to form a 5- to 7-member heterocycloalkyl ring having from 1-3 heteroatoms including, but not limited to, N, O and S. For example, $R^d$ and $R^e$, when attached to the same nitrogen atom can form a pyrrolidine, pyrrolidinone, piperidine, or morpholine ring, and the like. $R^f$ is a functional group including, but not limited to, of $C_{1-6}$ alkyl, $C_{1-6}$ haloalkyl, $C_{3-8}$ cycloalkyl, $C_{2-6}$ alkenyl, $C_{0-6}$ alkyl-aryl and $C_{0-6}$ alkyl-heteroaryl.

In Formula I, the subscripts m and n are independently selected and are integers from 0 to 4. In one embodiment of Formula I, the subscript m is the integer 0; and the subscript n is the integer 1. In another embodiment of Formula I, the subscripts m and n are each the integer 1.

In Formula I, $R^3$ is a functional group including, but not limited to, hydrogen, $C_{1-8}$ alkyl, $C_{1-8}$ haloalkyl, $C_{3-8}$ cycloalkyl, $C_{1-8}$ acyl, $-SO_2-C_{1-8}$ alkyl, aryl-$C_{0-4}$ alkyl and heteroaryl-$C_{0-4}$ alkyl.

In Formula I, $R^4$, if present, is a functional group including, but not limited to, $C_{1-8}$ alkyl, halogen, $-NO_2$ and $-CN$.

In Formula I, o is an integer from 0 to 1.

In one embodiment of Formula I, $R^1$, if present, is a functional group including, but not limited to, halogen, $C_{1-8}$ alkyl and $C_{1-8}$ haloalkyl. Within this embodiment, $R^1$ is preferably selected from the group consisting of chloro, fluoro, bromo, methyl and trifluoromethyl.

In another embodiment of Formula I, $R^2$, if present, is a functional group including, but not limited to, halogen, $-C(O)OR^d$, $-C(O)NR^dR^e$, $-NR^dR^e$ and $OR^d$, wherein $R^d$ and $R^e$ are independently selected and are each a functional group including, but not limited to, hydrogen, $C_{1-6}$ alkyl and $C_{1-6}$ haloalkyl, or $R^d$ and $R^e$ when attached to the same nitrogen atom are optionally combined to form a 5- to 7-membered heterocycloalkyl ring having from 1-3 heteroatoms including, but not limited to, N, O and S. For example, $R^d$ and $R^e$, when attached to the same nitrogen atom can form a pyrrolidine, pyrrolidinone, piperidine, or morpholine ring and the like. Within this embodiment, $R^2$ is preferably selected from the group consisting of:

In yet another embodiment of Formula I, $R^2$ is $—C(O)OR^d$; $R^3$ is $C_{1-8}$ alkyl; the subscripts m and o are each the integer 0; and n is an integer from 1-2. In yet another embodiment of Formula I, n is the integer 1; and $R^2$ on the phenyl ring is substituted at a position meta to the nitrogen atom shown in Formula I. In a preferred embodiment of Formula I, n is the integer 1; and $R^2$ on the phenyl ring is substituted at a position para to the nitrogen atom shown in Formula I.

In yet another embodiment of Formula I, $R^3$ is a functional group including, but not limited to, $C_{1-8}$ alkyl, $C_{1-8}$ haloalkyl, $C_{1-8}$ acyl and $C_{1-4}$ alkyl-aryl. Within this embodiment, $R^3$ is preferably methyl, ethyl, acetyl or benzyl.

In a particularly preferred embodiment of the invention, the compounds of Formula I have the structure as set forth in SubFormula Ia

In SubFormula Ia, $R^1$, if present, is a functional group including, but not limited to, $C_{1-8}$ alkyl, $C_{1-8}$ haloalkyl, $C_{3-8}$ cycloalkyl, $C_{2-8}$ alkenyl, $C_{2-8}$ alkynyl, halogen, $—NO_2$, $—CN$, $—OR^a$, $—SR^a$ and $—NR^aR^b$, wherein $R^a$ and $R^b$ are each independently selected and are functional groups including, but not limited to, hydrogen, $C_{1-6}$ alkyl, $C_{1-6}$ haloalkyl, $C_{3-8}$ cycloalkyl, aryl-$C_{0-6}$ alkyl and heteroaryl-$C_{0-6}$ alkyl, or when $R^a$ and $R^b$ are attached to the same nitrogen atom, $R^a$ and $R^b$ can be optionally combined to form a 5- to 7-member heterocycloalkyl ring having from 1-3 heteroatoms including, but not limited to, N,O and S. For example, $R^a$ and $R^b$, when attached to the same nitrogen atom, can be combined to form a pyrrolidine, piperidine or morpholine ring, and the like.

In SubFormula Ia, $R^2$, if present, is a functional group including, but not limited to, $C_{1-8}$ alkyl, $C_{1-8}$ haloalkyl, $C_{3-8}$ cycloalkyl, $—NO_2$, $—CN$, halogen, $—C(O)R^d$, $—C(O)OR^d$, $—C(O)NR^dR^e$, $—NR^dR^e$, $—S(O)_2NR^dR^e$, $OR^d$, $SR^d$, and $—NR^dC(O)R^f$, wherein $R^d$ and $R^e$ are each independently selected and are a functional group including, but not limited to, hydrogen, $C_{1-6}$ alkyl, $C_{1-6}$ haloalkyl, $C_{3-8}$ cycloalkyl, $C_{2-6}$ alkenyl, aryl-$C_{0-6}$ alkyl and heteroaryl-$C_{0-6}$ alkyl, or when $R^d$ and $R^e$ are attached to the same nitrogen, $R^d$ and $R^e$ can be optionally combined to form a 5- to 7-member heterocycloalkyl ring having from 1-3 heteroatoms including, but not limited to, N, O and S. For example, $R^d$ and $R^e$, when attached to the same nitrogen atom can form a pyrrolidine, pyrrolidinone, piperidine, or morpholine ring, and the like. $R^f$ is a functional group including, but not limited to, $C_{1-6}$ alkyl, $C_{1-6}$ haloalkyl, $C_{3-8}$ cycloalkyl, $C_{2-6}$ alkenyl, $C_{0-6}$ alkyl-aryl and $C_{0-6}$ alkyl-heteroaryl.

In SubFormula Ia, the subscripts m and n are each independently selected and are integers from 0 to 4. In a preferred embodiment of subFormula Ia, the subscripts m and n are each 1.

In SubFormula Ia, $R^3$ is a functional group including, but not limited to hydrogen, $C_{1-8}$ alkyl, $C_{1-8}$ haloalkyl, $C_{3-8}$ cycloalkyl, $C_{1-8}$ acyl, $—SO_2—C_{1-8}$ alkyl, aryl-$C_{0-4}$ alkyl and heteroaryl-$C_{0-4}$ alkyl.

In yet another embodiment, the compounds of Formula I have a structure selected from the group consisting of:

-continued

In a preferred embodiment, the compound of Formula I has the structure (A)

B. Synthesis of Compounds

The compounds of the invention can be prepared, for example, by the synthetic routes shown in Schemes 1 and 2. In each scheme, X is a halide or other leaving group, and non-interferring substituents are provided as —R, —R', —R" and R'".

As shown in Scheme 1, 2-aryl-4-anilinothiazole compounds of the invention can be prepared by a two-step synthetic route utilizing a modified Hantzch-type synthesis of aryl thiazoles. In the first step, benzothioamide i, is heated with a-chloroamide ii to undergo a cyclization reaction to provide the thiazole iii. The anilino nitrogen atom of thiazole iii can be further alcylated upon treatment of iii with a base, such as sodium hydride, and an alkylating agent, such as an alkyl halide and the like, to produce the alkylated product iv. A skilled artisan would recognize various modifications to the synthetic route presented in Scheme 1 that would produce other compounds within the scope of the invention.

As shown in Scheme 2, other compounds of the invention, e.g., 4-aryl-2-anilinothiazoles, can be prepared utilizing the Hantzch synthesis of thiazoles. In step 1 of Scheme 2, thiourea v can be reacted with α-haloacetophenone vi under thermal conditions to provide the thiazole vii (a regioisomer of compound iii). Alkylation or acylation of the 2-amino-group of thiazole vii by the treatment of vii with a base followed by the addition of an alkylating or acylating reagent (R'''—X), such as an alkyl halide, an acyl halide, and the like, will provide additional thiazole compounds, e.g., compound viii, that are also within the scope of the present invention.

Scheme 2

IV. Use of the Compounds/Compositions to Induce Neuronal Cell Differentiation

The compositions of the present invention can be used to induce neuronal cell differentiation in mammalian cells. A mammalian cell is contacted with a compound of Formula I, whereupon the mammalian cell differentiates into a neuronal cell. The mammalian cell can be contacted with a compound of Formula I (or a composition thereof) either in vivo or in vitro.

A. In vivo Induction of Neuronal Cell Differentiation

The compounds of Formula I as well as compositions thereof can conveniently be used to induce neuronal cell differentiation in vivo. The compounds and compositions of the present invention are administered to an individual, e.g., a mammal such as a human, in an amount effective to induce differentiation of mammalian cells (i.e., neural progenitor cells or neural stem cells) into neuronal cells. In view of their ability to induce neuronal cell differentiation, the compounds of Formula I are useful for treating neural disorders and diseases, such as, e.g., Alzheimer's Disease, Parkinson's Disease, Multiple Sclerosis, Amyotrophic Lateral Sclerosis (ALS or Lou Gehrig's Disease), Huntington's Disease, Frontotemporal Dementia (Pick's Disease) and Prion Diseases.

The compounds of Formula I can also be used for treating neural disorders that arise after trauma or injury to the central or peripheral nervous system (e.g., the spinal cord, peripheral nerves, or brain).

One of skill in the art will appreciate that the compositions of the present invention can be used alone or in combination with other compounds and therapeutic regimens to treat neural diseases or disorders. For example, a compound of Formula I may be administered in conjunction with a cholinesterase inhibitor such as, e.g., Donepezil (Aricept), Galantamine (Razadyne), Rivastigmine (Exelon), or Tacrine (Cognex) or glutamate regulators such as, e.g., Memantine (Namenda).

An effective amount of the composition will be determined by the existence, nature, and extent of any adverse side-effects that accompany the administration of the composition; the LD50 of the composition; and the side-effects of the composition at various concentrations. Typically, the amount of the composition administered will range from about 0.01 to about 20 mg per kg, more typically about 0.05 to about 15 mg per kg, even more typically about 0.1 to about 10 mg per kg body weight.

The compositions can be administered, for example, by intravenous infusion, orally, intraperitoneally, or subcutaneously. The formulations of compounds can be presented in unit-dose or multi-dose sealed containers, such as ampoules and vials.

The compositions of the present invention are typically formulated with a pharmaceutically acceptable carrier before administration to an individual or subject. Pharmaceutically acceptable carriers are determined, in part, by the particular composition being administered (e.g., Compound A), as well as by the particular method used to administer the composition. Accordingly, there are a wide variety of suitable formulations of pharmaceutical compositions of the present invention (see, e.g., Remington's Pharmaceutical Sciences, 17th ed., 1989).

Formulations suitable for oral administration can consist of (a) liquid solutions, such as an effective amount of the compound of Formula I suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of the following: lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compositions of the present invention may be in formulations suitable for other routes of administration, such as, for example, intravenous infusion, intraperitoneally, or subcutaneously. The formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

The dose administered to a patient, in the context of the present invention should be sufficient to effect a beneficial therapeutic response in the patient over time. For example, if the compositions of the present invention are administered to treat or prevent neural diseases or disorder, the dose administered to the patient should be sufficient to prevent, retard, or reverse symptoms associated with the neural disease or disorder (e.g., loss of motor control). The dose will be determined by the efficacy of the particular composition employed and the condition of the patient, as well as the body weight or surface area of the patient to be treated. The size of the dose also will be determined by the existence, nature, and extent of any adverse side-effects that accompany the administration of a particular composition in a particular patient.

B. In vitro Induction of Neuronal Differentiation

The compounds and compositions of the present invention can conveniently be used to induce neuronal differentiation in vitro. Mammalian cells are contacted with the compositions, whereupon the mammalian cells differentiate into neuronal cells.

1. Suitable Cells

The mammalian cells can be stem cells, typically neural progenitor cells. Methods for isolation and differentiation of human and animal neural stem cells have been described (see, e.g., U.S. Pat. Nos. 6,787,355; 6,680,198; 6,541,247; 6,497,872; 6,468,794; 6,294,346; 6,238,922; 6,165,783; 6,103,530; 5,968,829; and 5,928,947; and Gage, *Science* 287: 1433 (2000)).

Suitable cell for use in the methods of the present invention include, for example, stem cells such as neural progenitor cells derived from the hippocampus (e.g., from the dentate gyrus), the hypothalamus, the olfactory placode, subcortical white matter, subventricular zone, and spinal cord (see, e.g., Markakis et al., *J. Neuroscience* 24(12):2886 (2004); and Nunes et al., *Nature Medicine* 9(4):439 (2003); and Gage, *Science* 287:1433 (2000)). Typically, cells from a tissue specimen containing neural progenitor cells are cultured in growth medium containing growth factors that (1) stimulate stem cell growth without differentiation, and/or (2) allow for the selective adherence of only the stem cells to a ubstrate surface. After culturing the cells for a suitable amount of time, non-adherent matter is removed from the substrate surface, thus providing an expanded population of stem cells. Thus, homogeneous stem populations are obtained by positive selection of adherent cells.

The cells to be differentiated into neuronal cells can be derived from any suitable mammal. For example, the cells may be obtained from a rodents such as, for example, mice, rats, guinea pigs, and rabbits; non-rodent mammals such as, for example, dogs, cats, pigs, sheep, horses, cows, and goats; primates such as, for example, chimpanzees and humans. The cells to be differentiated may be primary cells or may be cells maintained in culture. If the cells are maintained in culture, they are typically contacted with the compounds/compositions of the present invention between the 12th and 15th passage in culture. Techniques and methods for establishing a primary culture of cells for use in the methods of the invention are known to those of skill in the art (see, e.g., Humason, ANIMAL TISSUE TECHNIQUES, 4th ed., W. H. Freeman and Company (1979), and Ricciardelli et al., (1989) *In Vitro Cell Dev. Biol.* 25: 1016.

2. General Culturing Methods

The mammalian cells may be contacted with a compound of Formula I (e.g., Compound A) alone or in the presence of other growth factors. Typically, the additional growth factors are BMP and LIF. Those of skill in the art will appreciate that the amount of the compound and growth factors can be adjusted to facilitate induction of differentiation in particular cell types. For example, the amount of Compound A is typically from about 0.1 µM to about 100 µM, more typically from about 0.25 µM to about 75 µM, even more typically from about 0.5 µM to about 50 µM, yet more typically about 1 µM to about 25 µM. Typically, the amount of RA protein contacted with the cells is from about 0.01 µM to about 100 µM, more typically from about 0.05 µM to about 50 µM, even more typically from about 0.075 µM to about 25 µM, yet more typically from about 0.1 µM to about 2 µM.

This aspect of the present invention relies upon routine techniques in the field of cell culture. Suitable cell culture methods and conditions can be determined by those of skill in the art using known methodology (see, e.g., Freshney et al., CULTURE OF ANIMAL CELLS (3rd ed. 1994)). In general, the cell culture environment includes consideration of such factors as the substrate for cell growth, cell density and cell contract, the gas phase, the medium, and temperature.

Incubation of cells is generally performed under conditions known to be optimal for cell growth. Such conditions may include, for example, a temperature of approximately 37° C. and a humidified atmosphere containing approximately 5% $CO_2$. The duration of the incubation can vary widely, depending on the desired results. In general, incubation is preferably continued until the cells express suitable proliferation. Proliferation is conveniently determined using BrdU labeling or $^3H$ thymidine incorporation.

Plastic dishes, flasks, or roller bottles may be used to culture cells according to the methods of the present invention. Suitable culture vessels include, for example, multi-well plates, petri dishes, tissue culture tubes, flasks, roller bottles, and the like.

Cells are grown at optimal densities that are determined empirically based on the cell type. Cells are typically passaged 12-15'times and discarded after 15 passages.

Cultured cells are normally grown in an incubator that provides a suitable temperature, e.g., the body temperature of the animal from which is the cells were obtained, accounting for regional variations in temperature. Generally, 37° C. is the preferred temperature for cell culture. Most incubators are humidified to approximately atmospheric conditions.

Important constituents of the gas phase are oxygen and carbon dioxide. Typically, atmospheric oxygen tensions are used for cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1-10% in the incubator. The preferred $CO_2$ concentration typically is 5%.

Defined cell media are available as packaged, premixed powders or presterilized solutions. Examples of commonly used media include, but are not limited to, N2, MEM-α, DME, RPMI 1640, DMEM, DMEM/F12, Iscove's complete media, or McCoy's Medium (see, e.g., GibcoBRL/Life Technologies Catalogue and Reference Guide; Sigma Catalogue). Typically, MEM-α or DMEM are used in the methods of the invention. Defined cell culture media are often supplemented with 5-20% serum, typically heat inactivated serum, e.g., human, horse, calf, and fetal bovine serum. Typically, 10% fetal bovine serum is used in the methods of the invention. The culture medium is usually buffered to maintain the cells at a pH preferably from about 7.2 to about 7.4. Supplements for neural cell media typically include, e.g., fibroblast growth factor (FGF), fibronectin, collagen, laminin I, and basement membrane extracts. Other supplements to the media typically include, e.g., antibiotics, amino acids, and sugars, and growth factors.

C. Detection of Neuronal Cell Differentiation

After administration of the compounds or compositions of the present invention in vivo or in vitro, induction of neuronal differentiation can be detected by detecting expression of neuron-specific proteins, detecting downregulation of neural progenitor cell-specific proteins, and detecting expression of neuron-specific transcription factors. Neuron-specific proteins include, for example, NeuroD1, NeuN, activated leukocyte cell adhesion molecule (ALCAM/CD166), CD90/Thy1, glutamate decarboxylases (i.e., GAD1/GAD67 and GAD2), Glut1, microtubule-associated protein-2 (MAP2), neural cell adhesion molecule 1 (NCAM-L1), Nectin-2/CD112, neural filament (NF), neurofilament H (NF-H), light neurofilament (NF-L), noggin, α-secretase, β-secretase, γ-secretase, tau, β-III tubulin (TuJ1), tyrosine hydroxylase, and neuron specific enolase. Typically, expression of NeuroD1 or NeuN is detected as an indicator of neuronal differentiation. Neuron specific transcription factors include, for example, E2F4 or RelA NF-kappa B.

1. Detection of Neuron-Specific Proteins

Expression of neuron-specific proteins may be detected by measuring the level of the neuron-specific protein or mRNA. The level of particular neuron-specific proteins can conveniently be measured using immunoassays such as immunohistochemical staining, western blotting, ELISA and the like with an antibody that selectively binds to the particular neuron-specific proteins or a fragment thereof. Detection of the protein using protein-specific antibodies in immunoassays is known to those of skill in the art (see, e.g., Harlow & Lane, Antibodies: A Laboratory Manual (1988), Coligan, Current Protocols in Immunology (1991); Goding, Monoclonal Antibodies: Principles and Practice (2d ed. 1986); and Kohler & Milstein, Nature 256:495-497 (1975). For measurement of mRNA, amplification, e.g., RT-PCR, LCR, or hybridization assays, e.g., northern hybridization, RNAse protection, dot blotting, are preferred. The level of protein or mRNA is detected, for example, using directly or indirectly labeled detection agents, e.g., fluorescently or radioactively labeled nucleic acids, radioactively or enzymatically labeled antibodies. These assays are well-known to those of skill in the art and described in, e.g., Ausubel, et al. ed. CURRENT PROTOCOLS IN MOLECULAR BIOLOGY (2001).

Typically, expression of the neuron-specific-proteins, NeuroD1 or NeuN, is used to detect differentiated neuronal cells. Expression of NeuroD1 and/or NeuN is correlated with neuronal cell differentiation. For direct inununohistochemical staining of cells to detect NeuroD or NeuN, cells are seeded in assay plates (e.g., 96 well plates) at a suitable density and treated with an appropriate amount of a compound of Formula I (e.g., Compound A), either alone or with other growth factors (e.g., RA) for an appropriate time. Cells are fixed in a 10% formalin solution. The fixed cells are washed again and stained with a reagent specific for NeuroD1 and/or NeuN (e.g., an antibody specific for NeuroD1 and/or NeuN) using methods known to those of skill in the art (see, e.g., Harlow & Lane, 1988, supra; Coligan, 1991, supra; Coding, 1986, supra; and Kohler & Milstein, 1975, supra). Photographic images of the cells are taken and NeuroD1 and/or NeuN-positive cells are counted manually from the images.

2. Detection of Neuron-Specific Transcription Factors

Expression of neuron-specific transcription factors can be detected using reporter gene assays. These assays are well known to those of skill in the art and are described in, e.g., Ausebel et al., supra. For example, expression of the neuron-specific transcription factor E2F4 or RelA NF-kappa B can be used to detect neuronal cell differentiation (see, e.g., Persengiev et al., Mol. Cell Biol. 19(9):6048-56 (1999) and Barkett et al., Oncogene 18(49):6910-24 (1999)). E2F4 actively promotes both the establishment as well as the maintenance of the neuronal phenotype (see, e.g., Persengiev et al., Mol. Cell Biol. 19(9):6048-56. 1999)).

Reporter genes, such as, for example, chloramphenicol acetyltransferase, firefly luciferase, bacterial luciferase, or β-galactosidase can be used in the reporter gene assays. The reporter construct is typically transiently or stably transfected into a cell. The promoter region of the relevant gene is typically amplified by PCR appropriate primers. The resulting PCR product is inserted into a suitable cloning vector, amplified and sequenced. The resulting plasmid is digested with appropriate restriction enzymes and the resulting fragment is inserted into a vector comprising a reporter gene.

a) Transiently Transfected Cells

For reporter gene assays with transiently transfected cells, the cells are typically seeded in a 6-well plate at a density of 30,000 cells/well in 2 mL of growth medium an incubated overnight or for a suitable time. Plasmid DNA is transfected into the cells using a suitable transfection reagent. After 8 hours, the transfected cells are plated into 96-well assay plates (e.g., Corning) and treated with an appropriate amount of a compound of Formula I (e.g., Compound A). The cells are incubated for 4 days, then the reporter gene activity in the cells is assayed using methods known to those of skill in the art.

b) Stably Transfected Cells

For reporter gene assays with stably transfected cells, the cells are typically seeded in a 6-well plate at a density of 30,000 cells/well in 2 mL of growth medium and incubated overnight or for a suitable time. An appropriate amount of reporter plasmid and a vector comprising a selectable marker (e.g., an antibiotic resistance gene) are co-transfected into the cells using an appropriate transfection reagent. After an appropriate incubation time, cells are seeded in a 10 cm culture dish and an appropriate amount of antibiotic is added to the culture medium. Fresh antibiotic is added at appropriate intervals. The antibiotic resistant colonies are pooled to yield the stably transfected cells. The transfected cells are plated into 96-well assay plates (e.g., Corning) and treated with an appropriate amount of a compound of Formula I (e.g., Compound A). The cells are incubated for 4 days, then the reporter gene activity in the cells is assayed using methods known to those of skill in the art.

D. Administration of Differentiated Neuronal Cells

Differentiated neuronal cells can be administered to a subject by any means known to those of skill in the art. In one embodiment of the invention, differentiated neuronal cells on an intact solid support (e.g., a three-dimensional matrix or a planar surface) can be administered to the subject, e.g., via surgical implantation. Alternatively, the differentiated neuronal cells can be detached from the matrix, i.e., by treatment with a protease, before administration to the subject, e.g., via intravenous, subcutaneous, or intraperitoneal routes.

In some embodiments of the present invention, stem cells (e.g., neural progenitor cells) are extracted from a human and subsequently contacted with a matrix for proliferation and differentiation into neuronal cells. Cells can be extracted from the subject to be treated, i.e., autologous (thereby avoiding immune-based rejection of the implant), or can be from a second subject, i.e., heterologous. In either case, administration of cells can be combined with an appropriate immunosuppressive treatment.

Neuronal cells differentiated according to the methods of the present invention may be administered to a subject by any means known in the art. Suitable means of administration include, for example, intravenous, subcutaneous, intraperitoneal, and surgical implantation.

The cells may be in formulations suitable for administration, such as, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

For surgical implantation, differentiated cells are typically left on an intact solid support, e.g., a three-dimensional matrix or planar surface. The matrix or planar surface is surgically implanted into the appropriate site in a subject. For example, a patient needing a neural graft can have differentiated cells on an intact solid support surgically implanted.

In determining the effective amount of the cells to be administered in the treatment or prophylaxis of conditions owing to diminished or aberrant neuronal cells, the physician evaluates cell toxicity, transplantation reactions, progression of the disease, and the production of anti-cell antibodies. For administration, neuronal cells differentiated according to the methods of the present invention can be administered in an amount effective to provide neuronal cells to the subject, taking into account the side-effects of the neuronal cells at various concentrations, as applied to the mass and overall health of the patient. Administration can be accomplished via single or divided doses.

EXAMPLES

The following examples are offered to illustrate, but not to limit, the claimed invention.

Example 1

Synthesis of Compound A

To a solution of thiobenzamide (1) (1.8 g, 13.1 mmol) in dimethylformamide (5 mL) was added ethyl 4-(2-chloroacetoamido)benzoate (2) (3.1 g, 12.8 mmol). The reaction mixture was stirred at 80° C. for 12 h. The organic solvent was then removed in vacuo. The crude product, ethyl 4-(2-phenylthiazol-4-ylamino)benzoate (3), was recrystallized in isopropanol. The resulting thiazole (3) (100 mg, 0.308 mmol) was added to a suspension of NaH (12 mg, 0.5 mmol) in tetrahydrofuran (5mL) at 0° C. and stirred for 10 min. To the reaction mixture was added excess $CH_3I$ (5 mmol), and the reaction mixture was stirred for 20 min and diluted with ethyl acetate. The organic layer was washed with brine, dried with $MgSO_4$, filtered and concentrated in vacuo. The residue was purified by flash column chromatography (silica gel, EtOAc/hexane, 1:7) to give A (94 mg, 90% yield) as a white solid. Compound A was crystallized in isopropanol/n-hexane. $^1$H-NMR (400 MHz, $CD_3CN$) δ 7.89 (m, 4h), 7.56 (m, 3H), 7.15 (dd, J=7.6, 2.76 Hz, 2H), 6.87 (s, 1H), 4.28 (q, J=7.2 Hz, 2H); 3.45 (s, 3H), 1.32 (t, J=7.2 Hz, 3H).

Example 2

Cell Culture and Neuronal Differentiation Detection Assays

Cell Culture: Neural precursor cells isolated from the hippocampus of adult female Fischer 344 rats[1] were maintained in N2 supplemented (Invitrogen) DMEM: Ham's F12 (Omega scientific) medium containing 20 ng/mL FGF-2 (PeproTech Inc.) HCN cells were expanded and maintained in an undifferentiated state on a polyornithine/laminin-coated dish in a defined serum-free growth medium (DMEM/F12 supplemented with N2 and 20 ng/ml bFGF) in a homogeneous monolayer. Neuronal and astroglial differentiation was analyzed directly with double-immunofluorescence staining of βIII tubulin (TuJ1) as a neuronal marker and glial fibrillary acidic protein (GFAP) as an astroglial marker. A combinatorial heterocycle library of 50,000 compounds was screened using undifferentiated, early passage HCN cells plated onto polyornithine/lamin-coated 384-well plates at a density of 6,000 cells/well in complete growth medium. After overnight incubation, the medium was exchanged with bFGF-free basal medium, and 5 µM of the compounds (final concentration) were added to each well. After treatment with compound for four days, cells were fixed and stained with βIII tubulin/TUJ1 and GFAP antibodies, the morphology of positively stained cells was analyzed, and the number of cells with the desired phenotypes was counted.

Immunocytochemistry: Cells were fixed with 4% paraformaldehyde for 30 min and washed with PBS, and then blocked for 1 hour at room temperature in PBS containing 0.3% Triton X-100 and 5% donkey serum (PBS-B). Samples were incubated in PBS-B containing dilutions (1:1500) of two primary antibodies for 24 hrs at 4° C., washed three times with PBS, and incubated w secondary antibodies conjugated to Cy3 (Jackson ImmunoResearch Laboratories, Inc.) Alexa Fluor 488 (Molecular Probe inc.). The samples then were treated with 1 µg/mL 4',6-diamidino-2-phenylindole (DAPI) for 30 min at room temperature, and then washed three times with PBS.

BrdU prohferation assay: Cells were treated with compounds (Compound A and RA). After 5 hours, the medium was changed and 10 µM of 5-bromo-2'-deoxy-uridine (BrdU) (final concentration) was added to each well. After treatment with BrdU for 2 hours, cells were fixed, washed three times with 0.1M Tris-buffer, and incubated in 2N HCl at 37° for 30 min. After treatment with 0.1M borate buffer (pH 8.5) for 10 min, cells were washed three times with PBS and treated with blocking buffer (PBS containing 0.3% Triton-X and 5% donkey serum) for 60 min. After overnight incubation with anti- BrdU (1:400) antibody, cells were washed with PBS and incubated with secondary antibody conjugated to Cy3 (1:1000) for 2 hours. After washing with PBS, BrdU-positive cells were counted.

RT-PCR: RT-PCR reactions were conducted using template DNAs synthesized according to the manufacturer's (invitrogen) instruction and the Superscript III first-strand synthesis system kit (cat. No. 18080-051, Invitrogen) and the following reaction mixtures:

5 µL 10×PCR buffer (200 mM Tris-HCl, pH 8.4, 500 mM KCl)
1 µL 10 mM dNTP mixture
1.5 µL 50 mM MgCl2
1 µL Primers (10 uM each)
1 µL Template DNA
0.2 µL Platinum Taq DNA polymerase (Invitrogen)
Distilled water to 50 µL The samples were incubated in a thermal cycler at 94° C. for 2 min and 26-32 cycles of PCR amplification were performed as follows: 94° C. for 30 seconds, 56° C. for 30 seconds, and 72° C. for 1 min.

The primers to detect NeuroD1 had the following sequences: gcaccatggacagctcccatgtctt (forward) and cctctaatcgtgaaagatggcatta (reverse). The primers to detect Sox2 had the following sequences: gaagaacagcccggaccgcgt-caaga (forward) and ettcatgtgcagagcgcgcagccgct (reverse)

Example 3

Identification of Compound A as a Compound the Selectively Induces Neuronal Differentiation To screen for small molecule inducers of neuronal differentiation, a primary neural progenitor cell culture (HCN) isolated from adult rat hippocampus was used. Although it has been shown that HCN cells can differentiate into neurons, astrocytes and oligodendrocytes in vitro, and can functionally integrate into existing neuronal networks in vivo, HCN cells very rarely differentiate into neuronal and astroglial lineages without treatment with exogenous factors, e.g., with RA or LIF in the absence of basic fibroblast growth factor, bFGF. (In contrast, a relatively large percentage of HCN cells are induced to differentiate into oligodendrocytes at high cell density by the insulin present in N2 supplemented medium.) This extremely low frequency of "spontaneous" (cell-autonomous) neuronal and astroglial differentiation of HCN cells makes them a good in vitro model system to screen for novel chemical regulators.

A combinatorial heterocycle library of 50,000 compounds was screened using undifferentiated, early passage HCN cells plated onto polyornithine/lamin-coated 384-well plates at a density of 6,000 cells/well in complete growth medium. After overnight incubation, the medium was exchanged with bFGF-free basal medium, and 5 µM of the compounds (final concentration) were added to each well. After treatment with compound for four days, cells were fixed and stained with βIII tubulin/TUJ1 and GFAP antibodies, the morphology of positively stained cells was analyzed, and the number of cells with the desired phenotypes was counted.

A class of 4-aminothiazoles was identified that induce specific neuronal differentiation in a dose-dependent manner. To further improve the potency and specificity of these compounds, a sublibrary of 4-aminothiazole compounds was generated by the reaction of α-chloro acetylanilines and thiobenzamides (Scheme 1), and their activity was assayed. Compound A had the highest activity among the analogues tested. The results of the structure-activity assays are set forth below.

| cmpd | R¹ | R² | R³ | Relative activity at EC$_{max}$* |
|---|---|---|---|---|
| 1 | H | p-COOEt | H | 10 |
| 2 | " | " | CH$_3$ | 100 |
| 3 | " | " | Et | 90 |
| 4 | " | " | Ac | 80 |
| 5 | " | " | Bn | Anti-proliferation (AP) |
| 6 | Cl | " | Ch$_3$ | 80 |
| 7 | CF$_3$ | " | " | 70 |
| 8 | H | m-COOEt | " | 20 |
| 9 | " | p-COOH | " | N/A |
| 10 | " | p-OCF$_3$ | " | 80 |
| 11 | " | p-Cl | " | 80 |
| 12 | " | p-NEt$_2$ | " | AP |
| 13 | " | p-C(O)NH-propyl | " | N/A |
| 14 | " | p-C(O)-morpholine | " | 90 |
| 15 | " | p-C(O)-pyrrolidine | " | 90 |

*Relative activities are expressed as EC$_{max}$ relative to Compound A, compound 2 (100) and DMSO (0 or no active, N/A)

Example 4

Compound A is a Potent Inducer of Neuronal Differentiation

Figure 1:
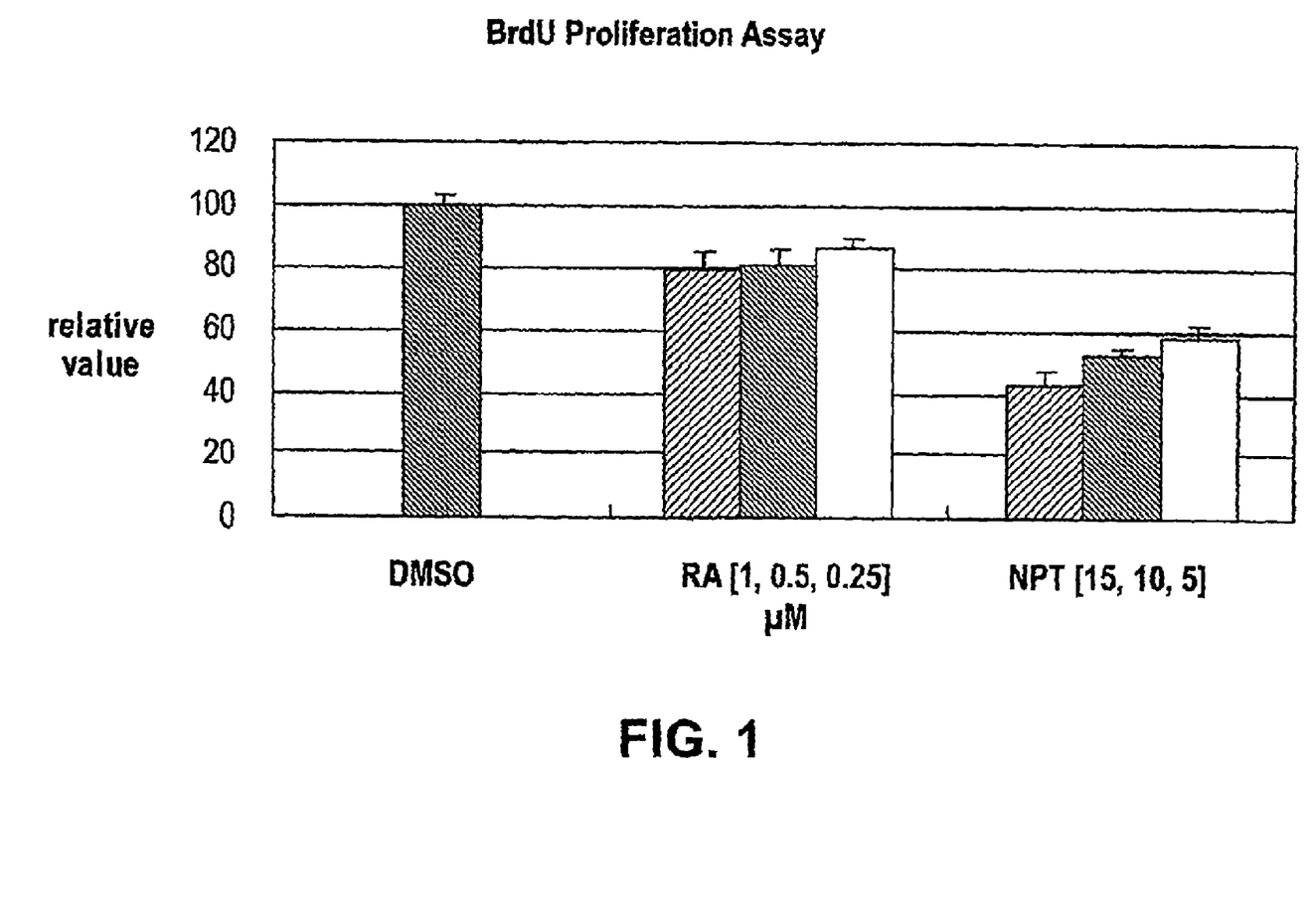
FIG. 1 illustrates data demonstrating that Compound A inhibits proliferation of hippocampal neural progenitor cells (HCN cells) treated with 1 μM, 0.5 μM and 0.25 μM RA or 15 μM, 10 μm and 5 μM Compound A for 5 hours in bFGF-free N2 medium were labeled with BrdU for 2 hours, and BrdU-positive cells were counted.
Figure 2:
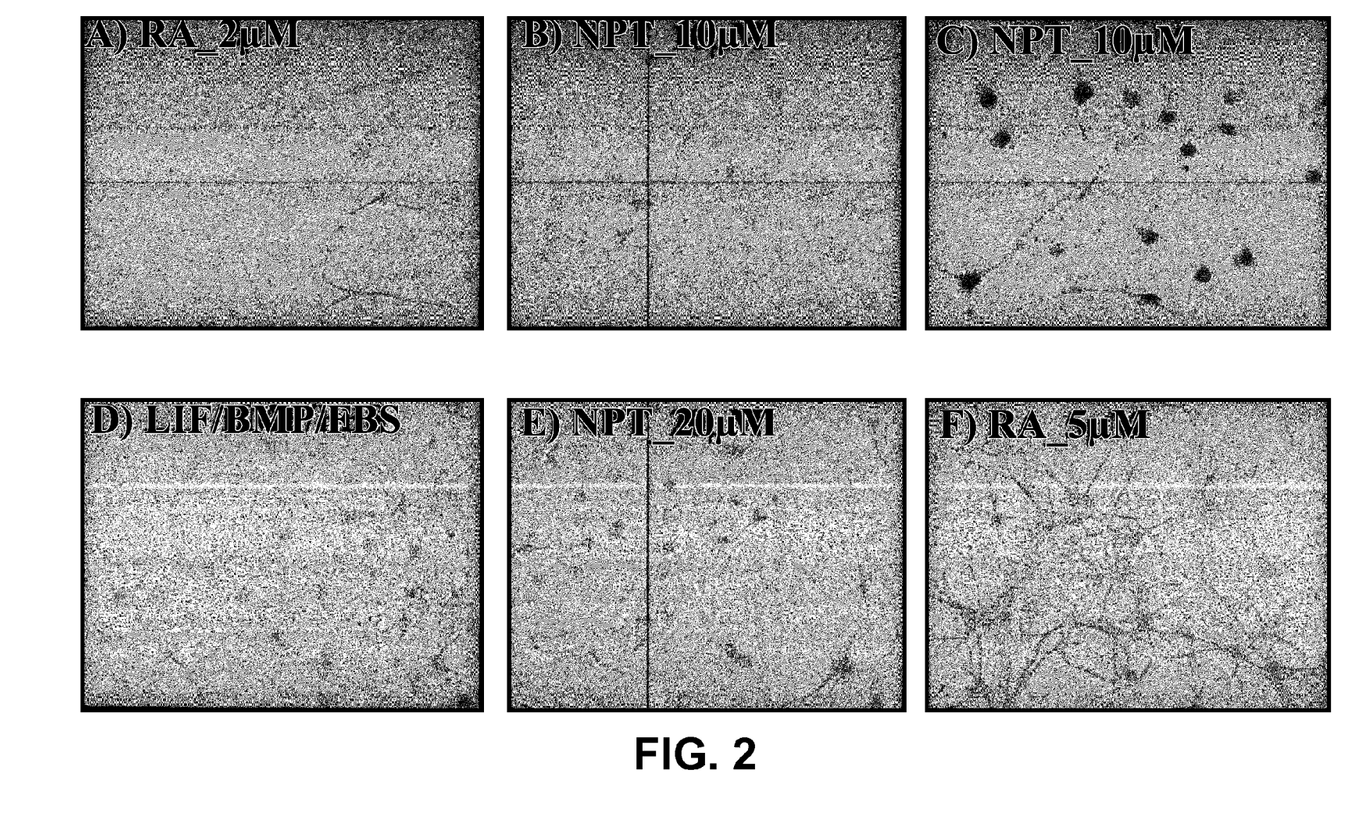
FIG. 2 illustrates data demonstrating that Compound A specifically induces neuronal differentiation of adult hippocampal neural progenitor cells (HCN cells). HCN cells in N2 media were treated with (A) 2 μM retinoic acid (RA) or (B) 10 μM of Compound A for four days and immunostained with TuJ1 (red) and GFAP (green) (C). Mature neurons were observed with Map2ab (red) and neurofilament-H (green) antibodies after seven days of treatment with 10 μM Compound A (D) Astroglial differentiation of HCN cells was strongly induced by LIF/BMP/FBS treatment (50 ng/ml LIF, 50 ng/ml BMP2 and 0.5% FBS) (E) Astroglial differentiation can be inhibited by compound A (20 μM), but not by RA (5 μM; F). Cells were stained with markers for neurons (TuJ1, red) and astrocytes (GFAP, green), and also with DAPI (blue) for nuclei.

Treatment of HCN cells with Compound A significantly slowed cell proliferation (FIG. 1) without visible cytotoxic effects; more than 90% of the cells differentiated into neuronal cells as determined by immunostaining with TuJ1 and the characteristic neuronal morphology. (Whereas RA showed weaker anti-proliferation activity and significant cytotoxicity over 2 µM in growth factor (bFGF or LIF/BMP2)-free basal medium.) GFAP-positive cells were very rarely detected after Compound A treatment, indicating that Compound A specifically induces a neuronal lineage (FIG. 2B). In contrast, relatively large numbers of both neuronal and astroglial cells were found with RA-induced differentiation of HCN cells, indicating that RA is not very specific (FIG. 2A). Longer treatment of HCN cells (seven days) with Compound A led to positive staining for later stage neuronal markers including neurofilament-H and Map2(a+b), indicating that Compound A-treated HCN cells can differentiate into mature neurons (FIG. 2C).

Figure 3:
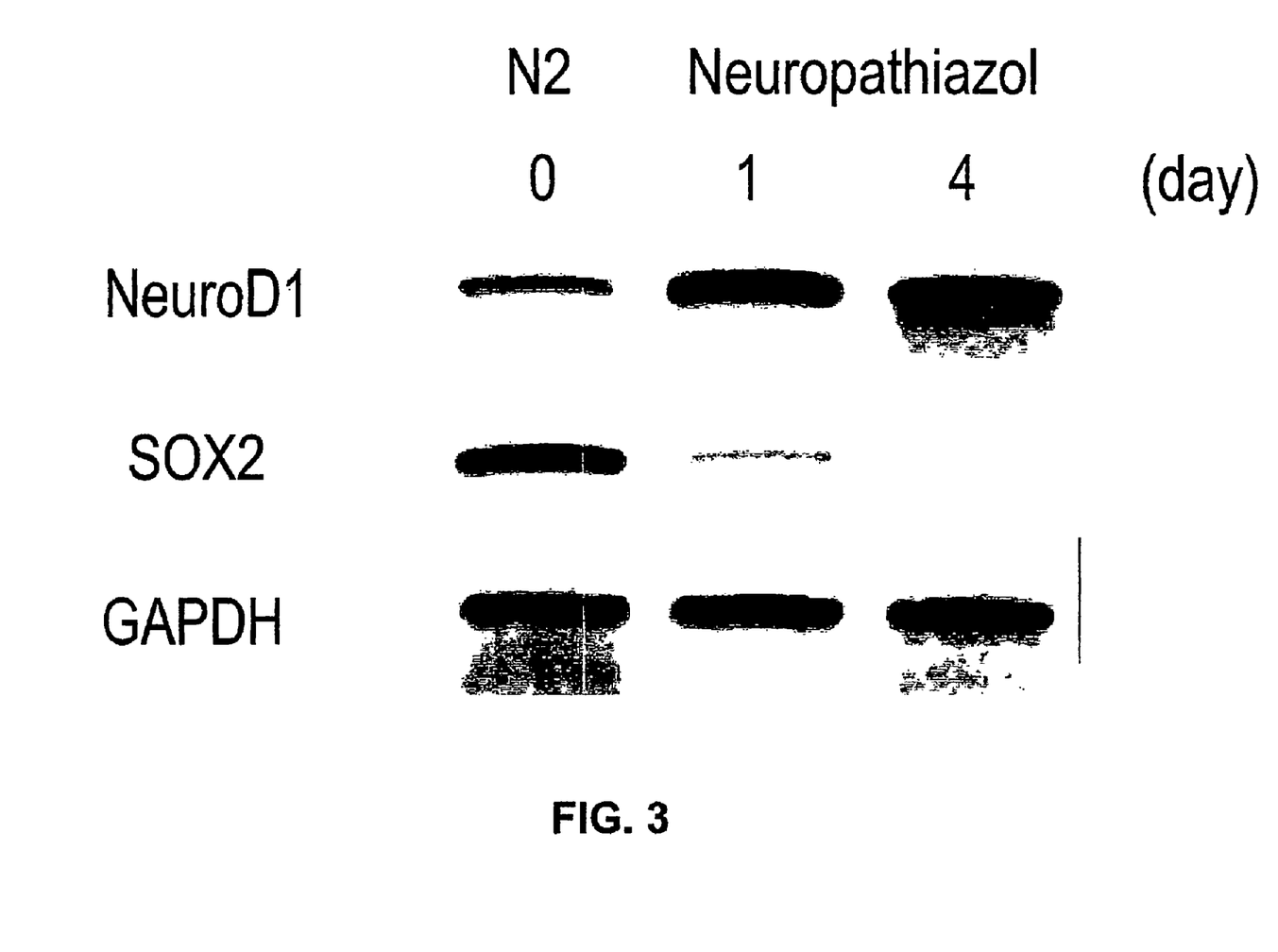
FIG. 3 illustrates data demonstrating that Compound A induces downregulation of Sox2, a neuronal progenitor cell marker and upregulation of NeuroD1, a neuronal cell marker. HCN cells were incubated with 10 μM Compound A or in compound-free N2 medium (N2; supplemented growth media without bFGF) and mRNA levels were determined by semi-quantitative RT-PCR analysis.

Moreover, RT-PCR of marker genes showed that Sox2 (a neural progenitor marker) (Kuwabara, T. et al., *Cell.* 116:779-793 (2004); Bylund, M. et al., *Nature Neurosci.*, 6:1162-8

(2003)) was down-regulated, and NeuroD1 (a neuronal cell marker) (Liu, M. et al., *Proc. Natl. Acad. Sci. USA.* 97:865-870 (2000)) was up-regulated upon treatment with Compound A (FIG. 3). Interestingly, Compound A can also inhibit astroglial differentiation induced by LIF and BMP2 (FIG. 2E), whereas RA cannot (FIG. 2F), suggesting that Compound A functions by a different mechanism and has more specific neurogenic-inducing activity than RA.

Figure 4:
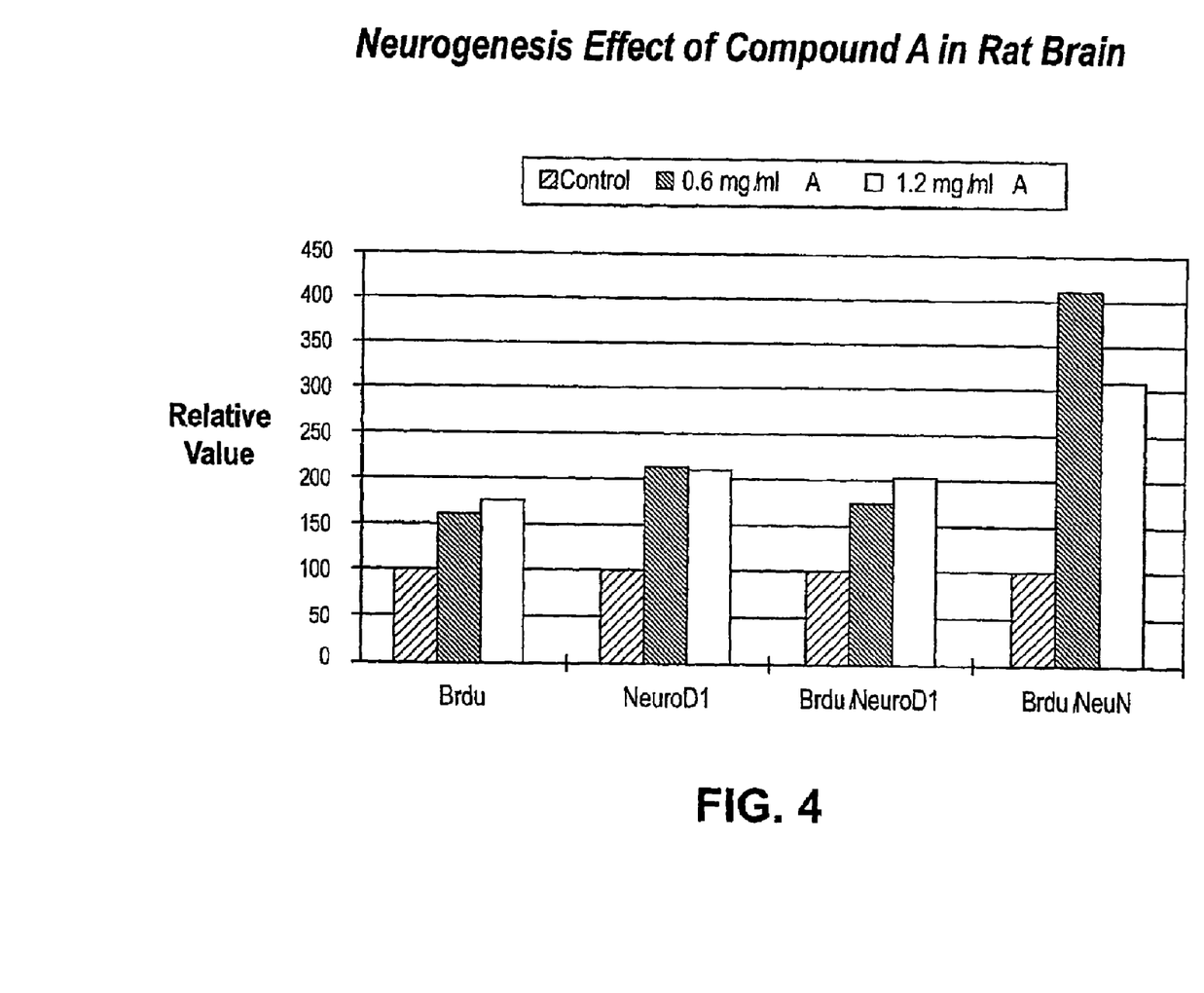
FIG. 4 illustrates data demonstrating that Compound A induces upregulation of the neuronal cell markers NeuroD1 and NeuN.

Finally, BrdU labeling in conjunction with immunocytochemistry to detect NeuroD1 and NeuN demonstrated that Compound A induces expression of neuron-specific marker genes and proliferation in HCN cells (FIG. 4).

The foregoing examples unequivocally establish that the compounds of the present invention (such as Compound A) induce neuronal differentiations.

In conclusion, a class of small molecules, represented by Compound A, has been identified as potent and selective agents for inducing neuronal cells differentiation. Compound A is a more selective inducer of neuronal differentiation than RA and can competitively suppress astrogliogenesis by LIF/BMP2/FBS in a dose-dependent manner. Compound A will be a useful tool for studying the molecular mechanisms that determine cell fate with the ultimate goal of stem cell therapy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the structure of Formula I:

and pharmaceutically acceptable salts, and hydrates thereof;
wherein: $R^1$, if present, is selected from the group consisting of: $C_{1-8}$ alkyl, $C_{1-8}$ haloalkyl, $C_{3-8}$ cycloalkyl, $C_{2-8}$ alkenyl, $C_{2-8}$ alkynyl, halogen, $-NO_2$, $-CN$, $-OR^a$, $-SR^a$ and $-NR^aR^b$; wherein $R^a$ and $R^b$ are each independently selected from the group consisting of: hydrogen, $C_{1-6}$ alkyl, $C_{1-6}$ haloalkyl, $C_{3-8}$ cycloalkyl, aryl-$C_{0-6}$ alkyl and heteroaryl-$C_{0-6}$ alkyl, or when $R^a$ and $R^b$ are attached to the same nitrogen, $R^a$ and $R^b$ can be optionally combined to form a 5- to 7-member heterocycloalkyl ring having from 1-3 heteroatoms selected from the group consisting of N, O and S;
$R^2$, if present, is selected from the group consisting of: $C_{1-8}$ alkyl, $C_{1-8}$ haloalkyl, $C_{3-8}$ cycloalkyl, $-NO_2$, $-CN$, halogen, $-C(O)R^d$, $-C(O)OR^d$, $-C(O)NR^dR^e$, $-NR^dR^e$, $-S(O)_2NR^dR^e$, $OR^d$, $SR^d$, and $-NR^dC(O)$ $R^f$; wherein $R^d$ and $R^e$ are each independently selected from the group consisting of: hydrogen, $C_{1-6}$ alkyl, $C_{1-6}$ haloalkyl, $C_{3-8}$ cycloalkyl, $C_{2-6}$ alkenyl, aryl—$C_{0-6}$ alkyl and heteroaryl-$C_{0-6}$ alkyl, or when $R^d$ and $R^e$ are attached to the same nitrogen, $R^d$ and $R^e$ can be optionally combined to form a 5- to 7-member heterocycloalkyl ring having from 1-3 heteroatoms selected from the group consisting of N, O and S; $R^f$ is selected from the group consisting of: $C_{1-6}$ alkyl, $C_{1-6}$ haloalkyl, $C_{3-8}$ cycloalkyl, $C_{1-6}$ alkenyl, $C_{0-6}$ alkyl-aryl and $C_{0-6}$ alkyl-heteroaryl;

m and n are each independently an integer from 0 to 4;
$R^3$ is a member selected from the group consisting of: $C_{1-8}$ alkyl, $C_{1-8}$ haloalkyl, $C_{3-8}$ cycloalkyl, $C_{1-8}$ acyl, $-SO_2-C_{1-8}$ alkyl, aryl-$C_{0-4}$ alkyl and heteroaryl-$C_{0-4}$ alkyl;
$R^4$, if present, is selected from the group consisting of: $C_{1-8}$ alkyl, halogen, $-NO_2$ and $-CN$; and
o is an integer from 0 to 1.

2. The compound of claim 1, wherein said compound has the formula wherein $R^1$, $R^2$, $R^3$, m and n are defined as set forth in claim 1.

3. The compound of claim 2, wherein m and n are each 1.

4. The compound of claim 3, wherein $R^2$ on the phenyl ring is para to the nitrogen atom shown in Formula I.

5. The compound of claim 1, wherein $R^1$ is selected from the group consisting of: halogen, $C_{1-8}$ alkyl and $C_{1-8}$ haloalkyl.

6. The compound of claim 5, wherein $R^1$ is selected from the group consisting of: chloro, fluoro, bromo, methyl and trifluoromethyl.

7. The compound of claim 1, wherein m is the integer 0.

8. The compound of claim 1, wherein $R^2$ is selected from the group consisting of: halogen, $-C(O)OR^d$ and $-C(O)NR^dR^e$, $-NR^dR^e$ and $OR^d$; wherein $R^d$ and $R^e$ are independently selected from the group consisting of: hydrogen, $C_{1-6}$ alkyl and $C_{1-6}$ haloalkyl, or $R^d$ and $R^e$ when attached to the same nitrogen atom are optionally combined to form a 5- to 7-membered heterocycloalkyl ring having from 1-3 heteroatoms selected from the group consisting of N, O and S.

9. The compound of claim 8, wherein $R^2$ is selected from the group consisting of:

10. The compound of claim 1, wherein $R^3$ is selected from the group consisting of: $C_{1-8}$ alkyl, $C_{1-8}$ haloalkyl, $C_{1-8}$ acyl and $C_{1-4}$ alkyl-aryl.

11. The compound of claim 10, wherein $R^3$ is selected from the group consisting of: methyl, ethyl, acetyl and benzyl.

12. The compound of claim 1, wherein $R^2$ is $-C(O)OR^d$ and $R^3$ is $C_{1-8}$ alkyl, m and o are each the integer 0, and n is an integer from 1-2.

13. The compound of claim 1, wherein the compound is selected from the group consisting of:

14. The compound of claim 13, wherein the compound is

15. A composition comprising the compound of any one of claims 1-14, and a pharmaceutically acceptable carrier.

* * * * *